United States Patent
Salvino et al.

(10) Patent No.: US 11,400,258 B2
(45) Date of Patent: Aug. 2, 2022

(54) SUTURELESS ADHESION SYSTEM

(71) Applicants: Chris Salvino, Scottsdale, AZ (US); Keir Hart, Lafayette, CO (US); Mark J. Huseman, Broomfield, CO (US)

(72) Inventors: Chris Salvino, Scottsdale, AZ (US); Keir Hart, Lafayette, CO (US); Mark J. Huseman, Broomfield, CO (US)

(73) Assignee: SharpMed, LLC., Scottsdale, AZ (US)

( * ) Notice: Subject to any disclaimer, the term of this patent is extended or adjusted under 35 U.S.C. 154(b) by 161 days.

(21) Appl. No.: 16/682,239

(22) Filed: Nov. 13, 2019

(65) Prior Publication Data

US 2020/0147348 A1    May 14, 2020

Related U.S. Application Data

(60) Provisional application No. 62/760,720, filed on Nov. 13, 2018.

(51) Int. Cl.
*A61M 25/02* (2006.01)

(52) U.S. Cl.
CPC ..... *A61M 25/02* (2013.01); *A61M 2025/0246* (2013.01); *A61M 2025/0266* (2013.01); *A61M 2210/101* (2013.01)

(58) Field of Classification Search
CPC .. A61M 2025/0246; A61M 2025/0266; A61M 2025/0273; A61M 2210/101; A61M 25/02
See application file for complete search history.

(56) References Cited

U.S. PATENT DOCUMENTS

| | | | |
|---|---|---|---|
| 4,324,237 A | 4/1982 | Buttaravoli | |
| 4,460,356 A | 7/1984 | Moseley | |
| 5,497,788 A | 3/1996 | Inman | |
| 5,707,348 A | 1/1998 | Krogh | |
| 6,124,521 A * | 9/2000 | Roberts | A61M 25/02 602/42 |
| 6,132,398 A | 10/2000 | Bierman | |
| 2007/0123828 A1 | 5/2007 | Propp | |
| 2008/0195050 A1 | 8/2008 | Dickert | |
| 2011/0009792 A1 | 1/2011 | Porat | |
| 2014/0046238 A1 | 2/2014 | Leibowitz | |
| 2016/0310053 A1 | 5/2016 | Warren | |

* cited by examiner

*Primary Examiner* — Deanna K Hall
(74) *Attorney, Agent, or Firm* — Kenneth Altshuler (57) ABSTRACT

A sutureless chest tube adhesion assembly configured to quickly and easily anchor a chest tube is described. The assembly generally comprises a notched flexible substrate adapted to adhere to human skin 415. A chest tube incision in a notched region of the substrate provides an entry point for the chest tube which is anchored to the substrate by way of an intermediate flexible membrane that covers and adheres to the chest tube and substrate. The intermediate flexible membrane has a matching notched region adapted to accommodate the chest tube. The chest tube and incision are adapted to be covered by a transparent cover sheet which covers and adheres to a portion of the substrate, the intermediate flexible membrane and to a portion of the human skin 415.

20 Claims, 9 Drawing Sheets

SUTURELESS ADHESION SYSTEM

CROSS-REFERENCE TO RELATED APPLICATIONS

This application claims priority to and the benefit of U.S. provisional Patent Application No. 62/760,720 entitled: Sutureless Adhesion System, filed on Nov. 13, 2018.

FIELD OF THE INVENTION

The present embodiments are directed to a chest tube anchoring system.

DESCRIPTION OF RELATED ART

The lungs are surrounded by a pleural sac made up of two membranes, the visceral and parietal pleurae. The parietal pleura lines the thoracic wall, and the visceral pleura surrounds the lung. The pleural space is a potential space between these two layers of pleurae. It contains a thin layer of serous pleural fluid that provides lubrication for the pleurae and allows the layers of pleurae to smoothly slide over each other during respiration. In abnormal circumstances the pleural space can fill with air and certain types of fluids not normally present requiring drainage.

In the industrialized world, trauma is the leading cause of death in males under the age of forty. In the United States, chest injuries are responsible for one-fourth of all trauma deaths. Many of these fatalities could be prevented by early recognition of the injury followed by prompt management. Some traumatic chest injuries require quick placement of chest tubes to drain out air and/or fluids (such as blood) from the chest cavity.

Several techniques are currently used to insert a chest tube, each of which involves a relatively lengthy manual procedure that requires knowledge and experience. The most common technique involves surgical preparation and draping at the site of the tube insertion (usually at the nipple level-fifth intercostal space, anterior to the mid-axillary line on the affected side), administering local anesthesia to the insertion site, and making a 2-4 cm vertical incision. A clamp is inserted through the incision and spread tearing muscle and tissue until a tract large enough to accept a finger is created. Next, the parietal pleura is punctured. One way is with the tip of a clamp, and the physician, on occasion, places a gloved finger into the incision to confirm the presence of a free pleural space locally. Next, the proximal end of the chest tube 145 is advanced through the incision into the pleural space. As the chest tube is inserted, it is sometimes directed posteriorly and superiorly towards the apex of the lung or elsewhere in the chest cavity. The goal is for the chest tube to drain the pleural space of both air and/or fluids such as blood. Accordingly, once the chest tube is appropriately in place to clear air and/or fluids (such as blood, infection, a transudate) from the pleural space, the tube is fixated to the skin 415 by with sutures around the tube anchoring the tube to the skin 415, dressing is applied, and the tube covered with a sterile dressing.

Insertion of a chest tube using this standard technique can require more than 15 minutes to accomplish by a physician, requires extensive medical training to be performed properly and can be extremely painful as it is a difficult area to anesthetize due to the intercostal nerve that runs on the bottom of every rib. Further, while performing the procedure, the physician must attend to the patient receiving the chest tube and thus is precluded from attending to other patients.

Figure 1A:
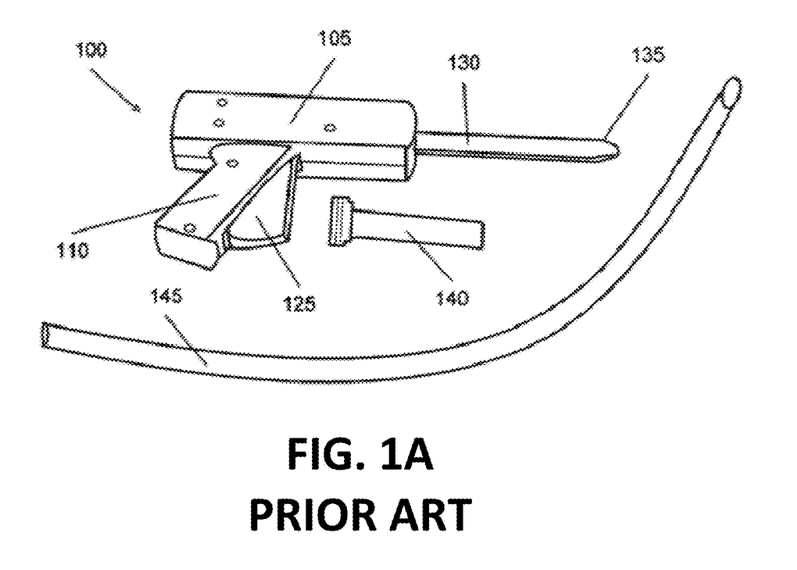
FIG. 1A is a line drawing that illustratively depicts a prior art chest tube insertion gun.

FIG. 1A depicts a prior art chest tube insertion gun 100 described in U.S. Pat. No. 7,811,293. This chest tube insertion gun 100 includes a housing 105, a handle 110 with the trigger 125, a probe tip 130 having a circular cutting tip 135 at the distal end thereof, a circular cross-sectioned cannula 140, a circular cross sectioned chest tube 145. The circular cutting tip 135 rotates outside of the distal end up to a 90° angle of rotation (rotation angle) from its neutral position before rotating back to its neutral position. The circular cutting tip 135 is also able to rotate a small negative angle from its neutral position in order to retract inside of the distal end of the probe tip 130. The rotation angle works well for the circular cross-sectioned cannula 140.

Figure 1B:
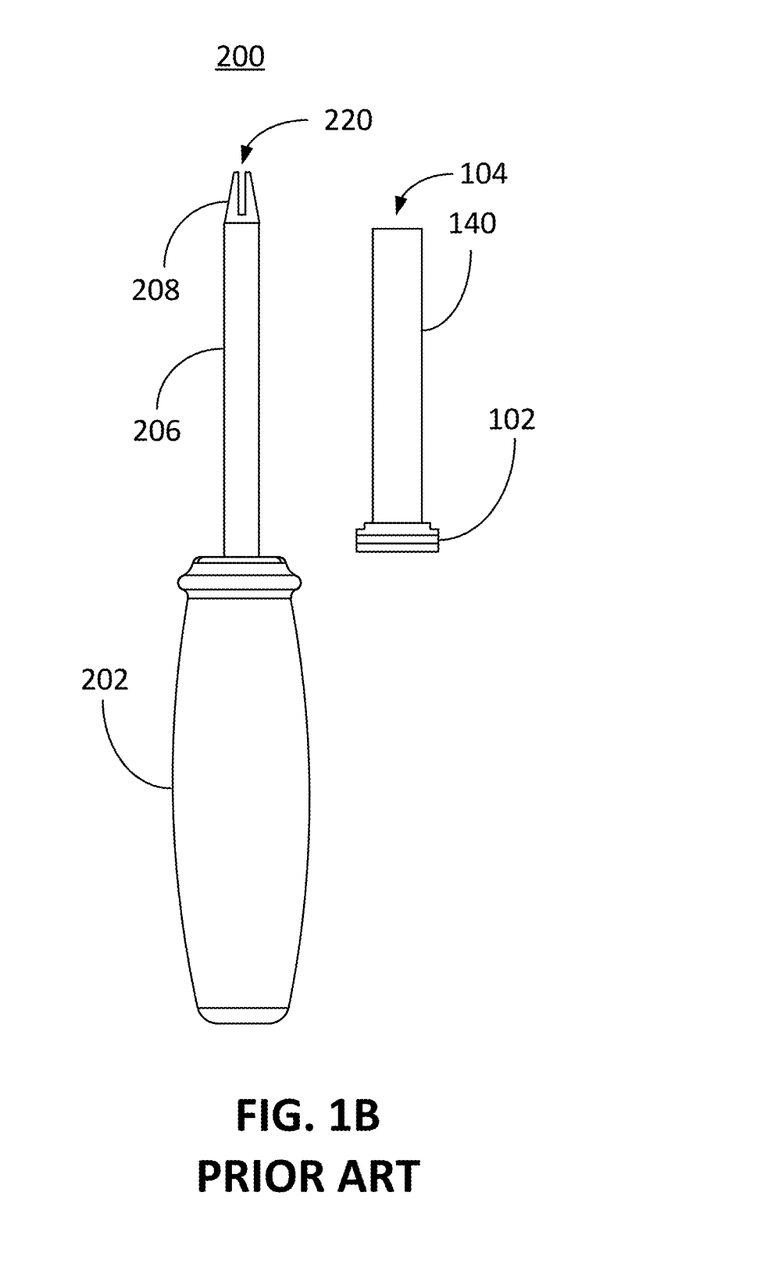
FIG. 1B is a line drawing that illustratively depicts a top view of the prior art actuator scalpel next to a prior art cannula.

FIG. 1B illustratively depicts a top view of another prior art actuator scalpel 200 next to a prior art cannula 140. The cannula 140 is a linear tube that is arranged to slide over the probe tip 208 and cover the probe shaft 206 via a base opening and platform 102 and a distal end opening 104. In practice, with the cannula 140 slid over the probe shaft 206, which essentially covers the probe 206, the actuator scalpel 200 is made to cut a pathway into the chest cavity of the patient whereby the cannula 140 is slid off of the probe tip 208 and thereby deployed into the chest of a patient. Accordingly, the probe 206 serves as a chest tube deployment shaft. The cannula 140 provides a pathway to feed a chest tube 145 into the chest cavity of the patient. The cannula 140 is typically removed by pulling over the chest tube 145 while the chest tube 145 is held in place by an operator. The chest tube is then sutured in place.

Figure 2A:
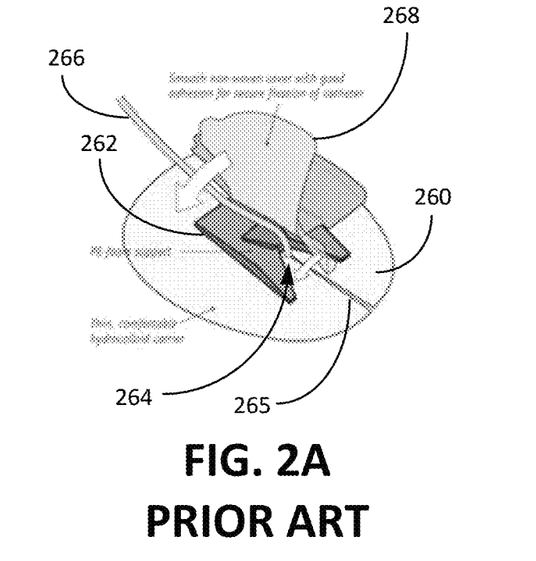
FIG. 2A illustratively depicts a perspective drawing of a prior art drain guard.

FIG. 2A is a prior art drain guard system from Copenhagen MedLab, of Copenhagen Denmark comprising a foam support 262 that goes over a base substrate/carrier 260. The foam support 262 is designed to position a drain line 266 at around 90° over an incision, as shown. A tube-line hole 264 also possesses a slit 265 that wraps around the drain line 266 at the incision point. An anchor bandage 268 holds everything in place. The problem with this system is that it is cumbersome with too many parts that need to be positioned just right. In an emergency situation, the system is considered to be problematic.

Figure 2B:
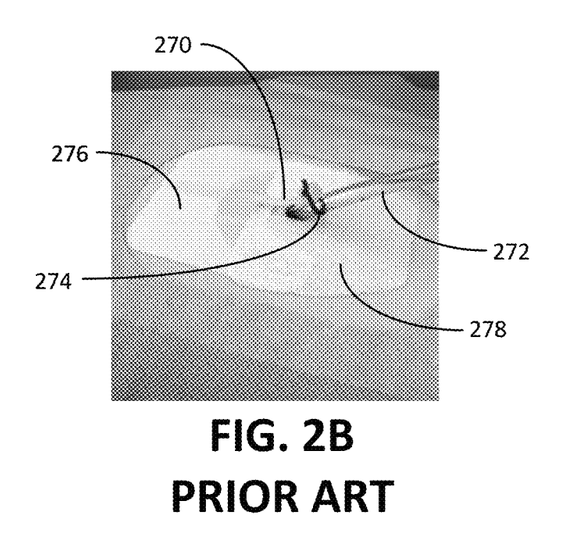
FIG. 2B illustratively depicts a prior art bandage system that wraps around and incision.

FIG. 2B is a prior art bandage system that wraps around and incision produced by Centurion Medical Products of Williamston, Mich. This bandage system provides three layers that essentially surrounds an incision. This bandage system possesses a mechanical anchor 270 integrated with an adhesive pad 276 that holds the tube 272 in place with a clip 274. A second bandage 278 forms an unobstructed opening around the incision with the adhesive pad 276. The problem with this bandage system is that it is cumbersome with too many parts that not only needs to be positioned just right, the incision is not intended to be covered because it would obstruct the clip 274. In an emergency situation, the system is considered to be problematic.

It is to innovations related to this subject matter that the claimed invention is generally directed.

SUMMARY OF THE INVENTION

The present embodiments are generally directed to a chest tube anchoring system with applications in a chest tube insertion device.

Certain embodiments of the present invention contemplate a sutureless adhesion system comprising: a flexible skin adhering substrate defined by a skin adhering substrate surface, a top substrate surface and a substrate periphery, the substrate periphery comprising a substrate incision framing notch at a substrate butting edge, the substrate incision framing notch sized to accommodate a chest tube diameter defined by a chest tube, the substrate incision framing notch defined by a substrate notch length and a substrate notch width greater than the chest tube diameter, the substrate incision framing notch configured to frame an incision in human skin through which the chest tube is adapted to penetrate; an intermediate flexible non-skin contacting membrane defined by a bottom membrane surface, a top membrane surface and a membrane periphery, the bottom membrane surface configured to only cover a portion of the flexible substrate and the chest tube when in the incision; a flexible cover sheet defined by a bottom sheet surface, a top sheet surface and a sheet periphery, the bottom sheet surface adapted to cover at least a portion of the top substrate surface and at least a portion of the top membrane surface; and adhesive covering at least a portion of the bottom substrate surface, the bottom membrane surface, and the bottom sheet surface, the flexible substrate adapted to adhere to human skin.

Yet other certain embodiments of the present invention contemplate a sutureless adhesion apparatus comprising: a flexible skin adhering substrate defined by a skin adhering substrate surface, a top substrate surface and a substrate periphery, the substrate periphery comprising a substrate incision framing notch at a substrate butting edge, the substrate incision framing notch unobstructely frames an incision that is capable of being made in human skin, a chest tube extending from the incision; an intermediate flexible non-skin contacting membrane defined by a bottom membrane surface with adhesive, a top membrane surface and a membrane periphery, the bottom membrane surface adhered to and covering nothing other than a portion of the flexible substrate and a portion of the chest tube; a flexible cover sheet defined by a bottom sheet surface, a top sheet surface and a sheet periphery, the flexible cover sheet adhered at least a portion of the top substrate surface and at least a portion of the top membrane surface, the skin adhering substrate surface and a portion of the bottom sheet surface configured to adhere to human skin.

While other certain embodiments of the present invention contemplate a method for stabilizing a chest tube, the method comprising: providing a flexible substrate pad possessing a substrate U-shaped notch located at a substrate pad edge; positioning the substrate U-shaped notch over an incision in a human chest; adhering the flexible substrate pad to human skin, the substrate U-shaped notch unobstructedly (i.e., without obstruction) framing the incision; inserting the chest tube in the incision; securing the chest tube to the substrate pad with an adhesive covered intermediate flexible membrane, nothing is between the chest tube and the flexible substrate pad when secured, the flexible membrane does not extend onto the human skin or over any portion of the substrate pad edge; and covering a portion of the intermediate flexible membrane over the substrate U-shaped notch and a portion of the human skin with an adhesive coated flexible cover sheet.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving similar uses of a sutureless attachment for tubes that are deployed in a human body. In what follows, similar or identical structures may be identified using identical callouts.

Described herein are embodiments of a sutureless chest tube attachment assembly configured to quickly and easily anchor a chest tube. Certain examples of the assembly generally comprises a notched flexible substrate adapted to adhere to human skin 415. A chest tube incision in a notched region of the substrate provides an entry point for the chest tube which is anchored to the substrate by way of an intermediate flexible membrane that covers and adheres to the chest tube and substrate. Some embodiments describe an intermediate flexible membrane has a matching notched region adapted to accommodate the chest tube. The chest tube and incision are adapted to be covered by a transparent cover sheet which covers and adheres to a portion of the substrate, the intermediate flexible membrane and to a portion of the human skin 415.

Figure 3A:
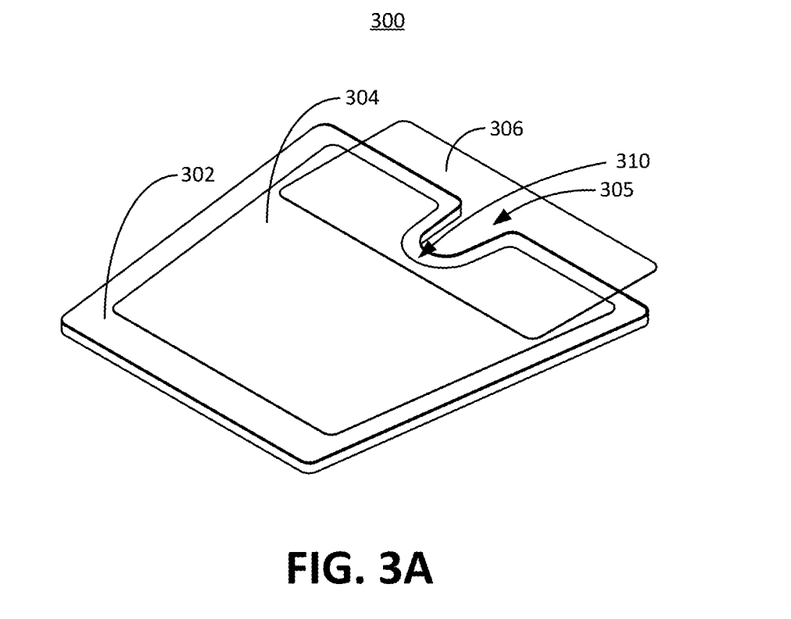
FIG. 3A is a line drawing that illustratively depicts a Sutureless Adhesion System consistent with embodiments of the present invention.

FIG. 3A illustratively depicts a line drawing of a Sutureless Adhesion System consistent with embodiments of the present invention. As shown, the present Sutureless Adhesion System 300 is generally comprised of a flexible substrate 302 that is adapted and arranged to adhere to a person's skin 415, an intermediate flexible membrane 304 adapted and arranged to adhere to the top surface of the flexible substrate 302, and a clear flexible coversheet 306 adapted to cover the notch regions 305 and 310. In this embodiment, the membrane notch 310 is sized to essentially frame the substrate notch 305 and the flexible substrate 302 is sized to essentially frame the intermediate flexible membrane 304. For example, membrane notch 310 partially surrounds the substrate notch 305 without overlapping the substrate notch periphery (see the dashed periphery 335 in the notch region 305, shown in FIG. 3C). Likewise, in the present embodiment, the flexible substrate 302 frames the intermediate flexible membrane 304 because the membrane periphery 355 follows the shape of the substrate periphery 335 without overlapping the substrate periphery 335. Accordingly, by framing, it is meant that one overlaying element may follow (either identically or sort of) the shape of the overlayed element without overlapping peripheries.

Figure 3B:
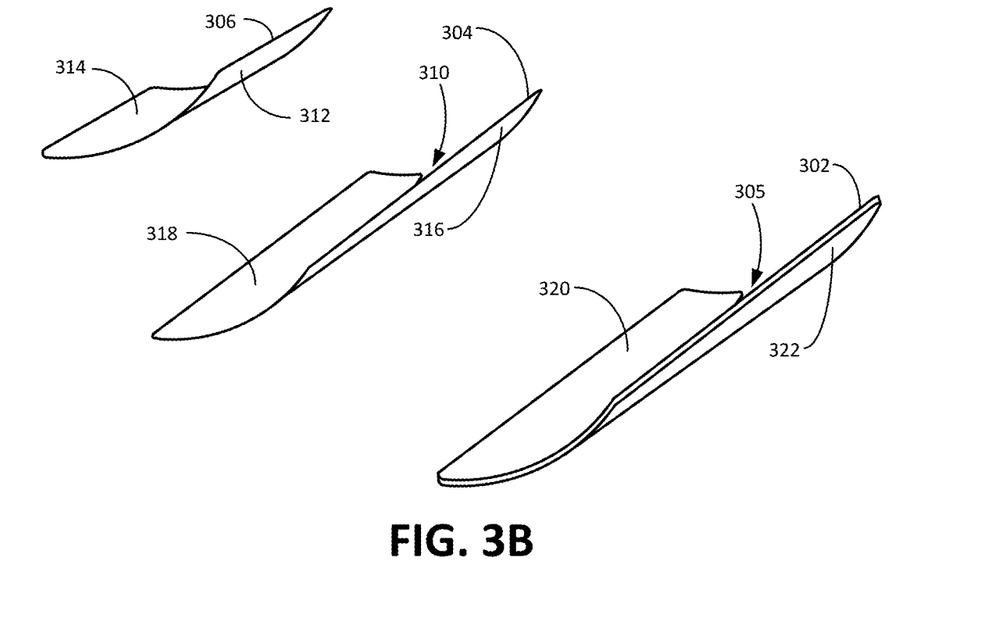
FIG. 3B illustratively depicts an exploded view line drawing of a Sutureless Adhesion System revealing the top surface and the bottom surface consistent with embodiments of the present invention.

FIG. 3B illustratively depicts an exploded view line drawing of a Sutureless Adhesion System 300 revealing the top surface 320 and the bottom surface 322 consistent with embodiments of the present invention. The flexible coversheet 306 (which is depicted as opaque in this view to help with the explanation) defines a top sheet surface 314 that in certain embodiments is devoid of any adhesive and a bottom sheet surface 312 that possesses adhesive. Certain embodiments envision the bottom sheet surface 312 being fully covered with adhesive while other embodiments envision the bottom sheet surface 312 being partly covered with adhesive. The intermediate flexible membrane 304 defines a top membrane surface 318 that in certain embodiments is devoid of any adhesive whatsoever and a bottom membrane surface 316 that possesses adhesive whereby certain embodiments envision adhesive entirely covering the bottom membrane surface 316. The flexible substrate 302 defines a top substrate surface 320 that in certain embodiments is devoid of any adhesive whatsoever and the bottom substrate surface 322, i.e., the skin adhering surface 322, that possesses adhesive which in certain embodiments is envision to be completely covered in adhesive, while in other embodiments does not completely cover the skin adhering surface 322. Certain embodiments envision that the adhesive on the bottom coversheet surface 312 is different than the adhesive on the bottom membrane surface 316 which is different than the bottom substrate surface 322 while other embodiments envision the adhesive all being the same. Certain other embodiments contemplate the adhesive on two of the three bottom surfaces being the same while one is different.

Figure 3C:
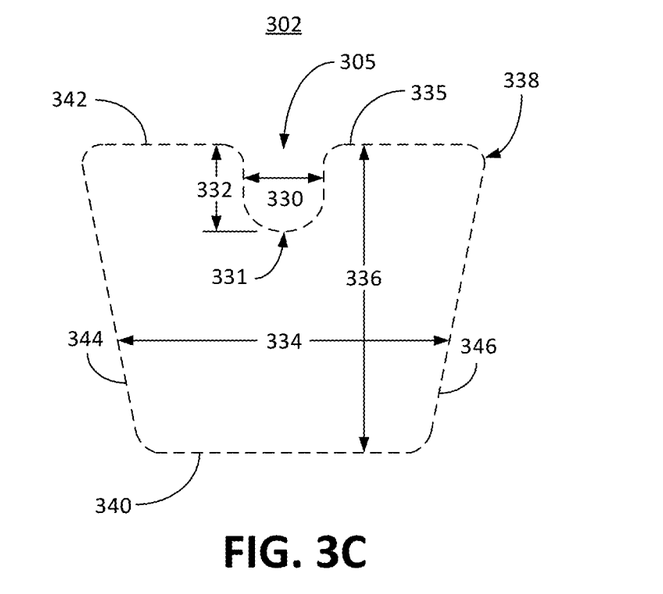
FIGS. 3C and 3D illustratively depicts line drawings defining geometries of the flexible substrate and the intermediate flexible membrane consistent with embodiments of the present invention.
Figure 3D:
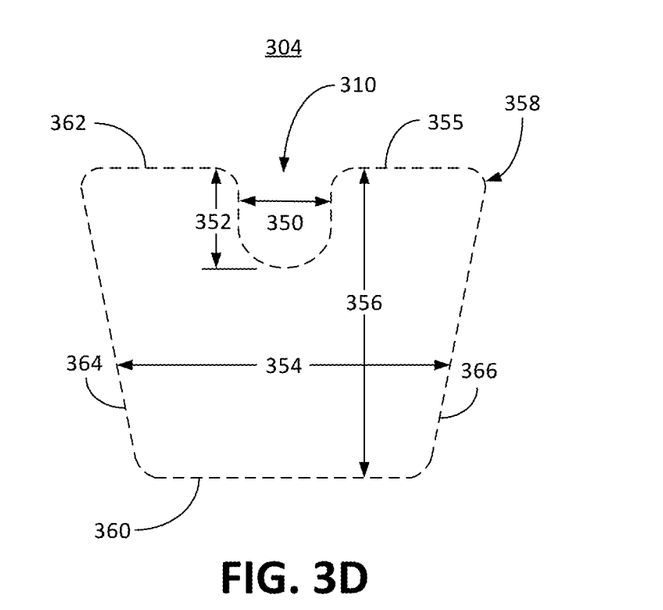

FIGS. 3C and 3D illustratively depicts line drawings defining geometries of the flexible substrate 302 and the intermediate flexible membrane 304 consistent with embodiments of the present invention. With reference to the flexible substrate 302 of FIG. 3C, the dashed line defines the substrate periphery 335, which is essentially trapezoid-shaped in the present embodiment. Certain other embodiments envision a square, rectangle or some other shape within the scope and spirit of the present invention. The two parallel sides of the trapezoid define the front side 342 and the back side 340 which also define the length 336 of the flexible substrate 302. The nonparallel sides 344 and 346 define the width 334 of the flexible substrate 302 in any given location along the nonparallel sides 344 and 346. In the present embodiments, the corners 338 are rounded, however other embodiments envision no such limitation. The front side 342 possesses a U-shaped substrate notch 305 with a substrate butting-edge 331 that is sized to accommodate the diameter of a chest tube (generally between 6.7 and 13.3 mm for adults, designated as a 20 Fr to 40 Fr (Fr for French catheter scale) in contrast to 6-26 Fr for children). Certain embodiments envision the substrate notch 305 being channel shaped or something other than U-shaped without departing from the scope and spirit of the present invention.

The U-shaped substrate notch 305 is defined by a notch length 332 and a notch width 330 which are both greater than the diameter of a selected chest tube. Certain embodiments envision that the notch length 332 and the notch width 330 have a standard size to accommodate a 40 Fr catheter tube or some other sized catheter tube. As will be discussed later, the U-shaped substrate notch 305 is adapted to accommodate an incision in human skin 415 through which the chest tube (not shown) is adapted to penetrate.

Likewise, with reference to the intermediate flexible membrane 304 of FIG. 3D, the dashed line defines the membrane periphery 355, which is essentially trapezoid-shaped in the present embodiment. As with the substrate, other embodiments envision a square, rectangle or some other shape within the scope and spirit of the present invention. The two parallel sides of the trapezoid are defined as the front side 362 in the back side 360 which further define the length 356 of the intermediate membrane 304. The nonparallel sides 364 and 366 define the width 364 of the intermediate membrane 304 in any given location along the nonparallel sides 364 and 366. In the present embodiments, the corners 358 are rounded however other embodiments envision no such limitation. The front side 362 possesses a U-shaped membrane notch 310 that is larger in length 352 and width 350 than the U-shaped substrate notch 305. As with the substrate notch 305, certain embodiments envision the membrane notch 310 being channel shaped or something other than U-shaped without departing from the scope and spirit of the present invention. Certain other embodiments envision the membrane notch 310 being essentially the same size (notch length and width) as the substrate notch 305. Certain embodiments envision the intermediate membrane periphery 355 fitting inside of the flexible substrate periphery 335, while other embodiments envision the intermediate membrane periphery 355 in the flexible substrate periphery 335 essentially being the same size or some other different size.

Figure 4A:
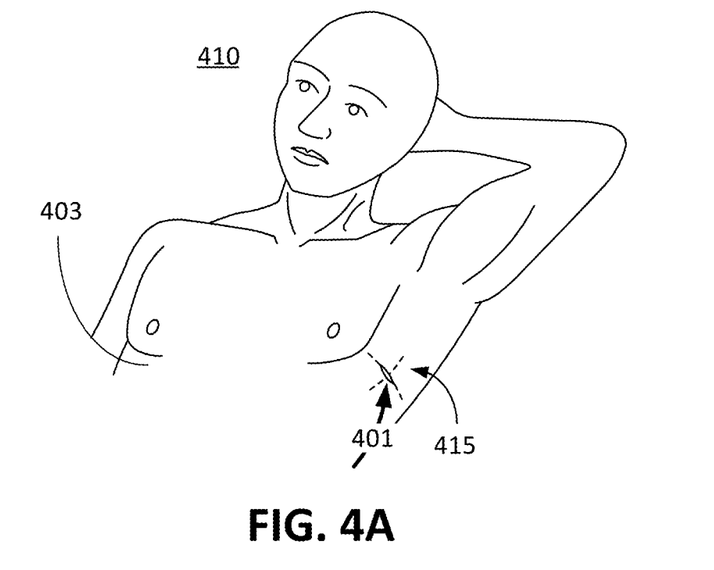
FIG. 4A is a line drawing that illustratively depicts a typical location where an embodiment of the chest tube can be deployed.
Figure 4B:
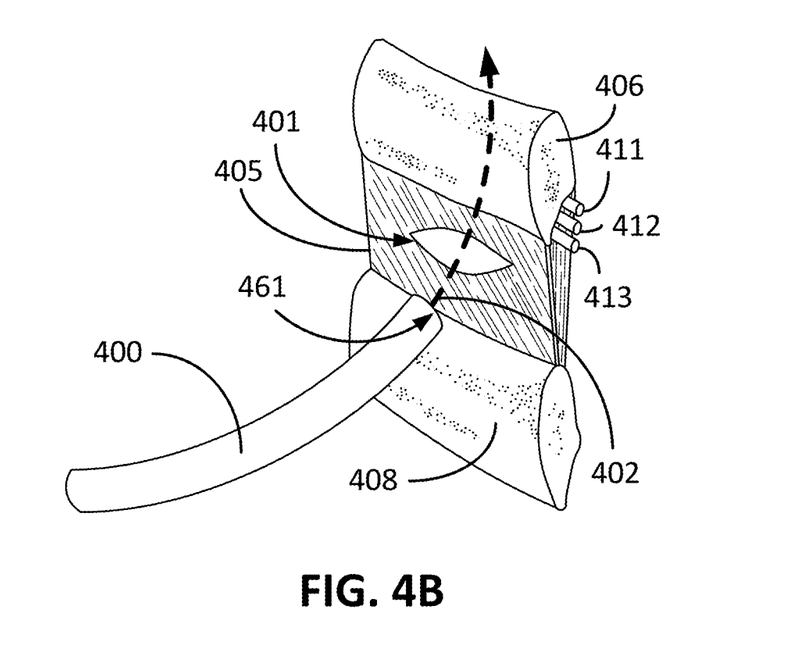
FIG. 4B is a line drawing that illustratively depicts one embodiment of a chest tube being inserted between ribs of a patient/subject consistent with embodiments of the present invention.

FIG. 4A illustratively depicts a typical location where an embodiment of the chest tube 400 can be deployed. As shown, the patient/subject 410 is marked with a dashed-X to better see the incision 401 pointing to a typical location at the fifth rib (under the armpit) where a chest tube 400 (or cannula) can be deployed. It is well known in the art that an entry point to the chest cavity 403 can be elsewhere depending on the issue at hand. The dashed-X and incision 401 in the cross point resides soundly in an optimal location to access the internal locations of the chest cavity 403 wherein fluid/air buildup can occur due to trauma, for example. FIG. 4B illustratively depicts one embodiment of a chest tube being inserted between ribs of a patient/subject consistent with embodiments of the present invention. Here, an incision 401 is made via a scalpel (such as a hand held scalpel or actuator scalpel 200 (not shown in this figure) in the intercostal muscles 405 between an upper rib 406 and a lower rib 408. Certain embodiments envision the chest tube 400 being oval in cross-section in order to fit more effectively between the ribs 406 and 408 while providing greater volume of liquid/air to drain out from buildup in the chest cavity 403. The intercostal artery 412 and the intercostal vein 411 are shown for reference. In practice either at the chest tube 400 is inserted directly into the incision 401 along the dashed arrow 402. Optionally, with reference to FIGS. 1A and 1B, a cannula 140 can be disposed over the probe shaft 206 so that the probe tip 208 is unobstructed for the scalpel blade to make the incision 401. The scalpel blade is not shown. Once the incision 401 is made, the probe tip 208 and probe shaft 206 are pressed into the chest cavity 403 up to the platform 102. The actuator scalpel 200 is then pulled out by one of the operator's/surgeon's hand while the other operator's/surgeon's hand holds the cannula 200 in place via the platform 102. Once deployed, the platform 102 can cover the incision 401 in order to seal the incision 401. In the present embodiment, the platform 102 can be covered and held in place with the Sutureless Adhesion System 300, or other embodiment of the Sutureless Adhesion System, whereby the cannula 140 can serve as a makeshift chest tube. Optionally, and conventionally, the chest tube 145 is fed through the cannula 140 into the chest cavity 403.

Figure 5:
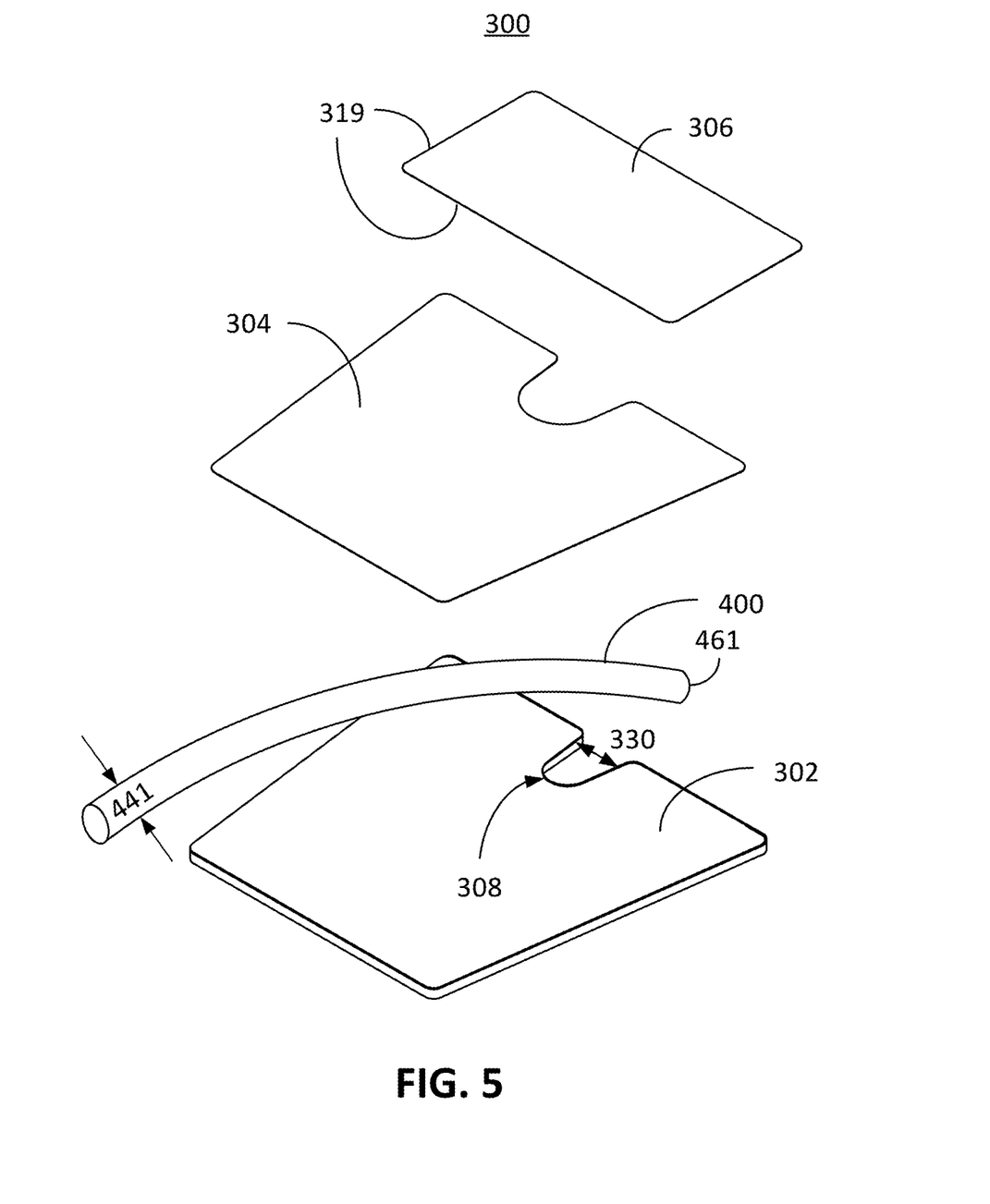
FIG. 5 is a line drawing that illustratively depicts drawings showing the general layout and position of the Sutureless Adhesion System with the chest tube in accordance with embodiments of the present invention.

FIG. 5 illustratively depicts drawings showing the general layout and position of the Sutureless Adhesion System 300 with the chest tube 400 in accordance with embodiments of the present invention. In certain commercial embodiments of the present invention, the flexible substrate 302 can be a closed-cell foam, such as a 1773 white closed-cell foam with an adhesive backing manufactured by 3M Corporation of St. Paul, Minn., rated for long-term contact with human skin 415. The flexible substrate 302 provides a cushioning layer to improve comfort when the chest tube 400 is pressed against the flexible substrate 302. As shown in this embodiment, there is nothing between the chest tube 400 and the flexible substrate 302. The diameter 441 of the chest tube 400 is shown here for reference. The intermediate flexible membrane 304 can be a 3M 4076 white nonwoven adhesive backed flexible layer. The intermediate flexible membrane 304 is specifically adapted to hold/retain the chest tube 400 essentially fixedly in place. Based on a 36 Fr catheter tube, the area of the intermediate flexible membrane 304 needs to be between 30 in$^2$ and 60 in$^2$ in order to provide retention of the chest tube comparable to being sutured in place. Based on a 14 Fr catheter tube, the area of the intermediate flexible membrane 304 needs to be approximately 20 in$^2$. Based on a 40 Fr catheter tube, the area of the intermediate flexible membrane 304 needs to be approximately 60 cm$^2$. As should be appreciated by those skilled in the art, a more thorough or different analysis may yield different numbers. The present use of adhesive bonding the intermediate flexible membrane 304 to the flexible substrate 302 improves times, reduces pain to a patient, increases consistency in tube 400 retention, just to name several advantages. Lastly, the clear flexible coversheet 306 can be a clear 3M Tegaderm adhesive backed membrane that protects the incision site while allowing medical personnel to effortlessly inspect incision 401. Moreover, the clear flexible coversheet 306 protects the incision external element, while somewhat sealing the incision site 401 from leaking bodily fluids therefrom. The flexible coversheet 306, which in certain embodiments is not clear, can cover both a portion of the flexible substrate 302 and a portion of the intermediate flexible membrane 304 as well as the skin 415 and the incision 401 as shown in FIG. 6D. As shown, the flexible coversheet periphery 319 is partially on the flexible substrate 302 and the intermediate flexible membrane 304.

Figure 6A:
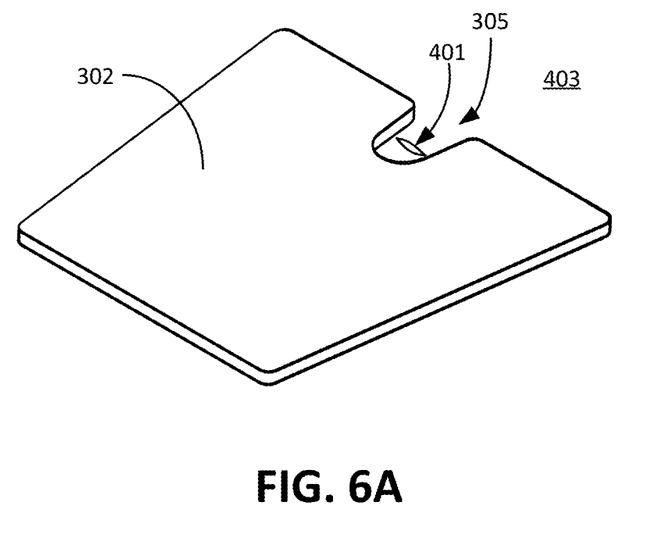
FIGS. 6A-6D are line drawings that illustratively depict a method for stabilizing a chest tube consistent with embodiments of the present invention.
Figure 6B:
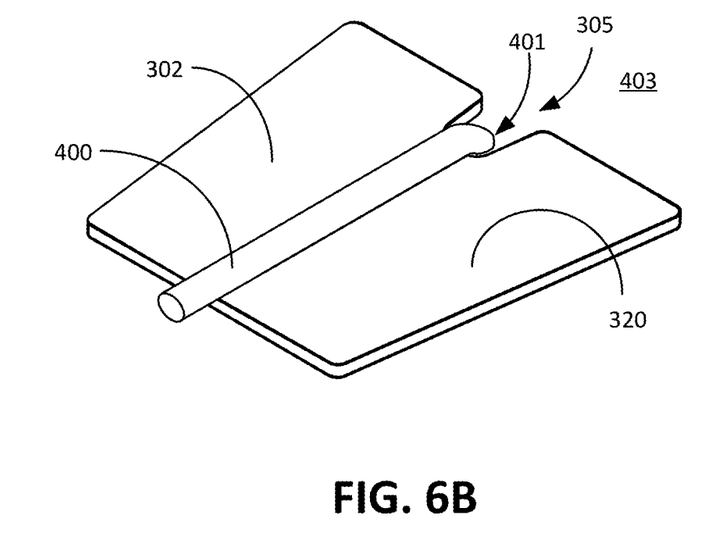
Figure 6C:
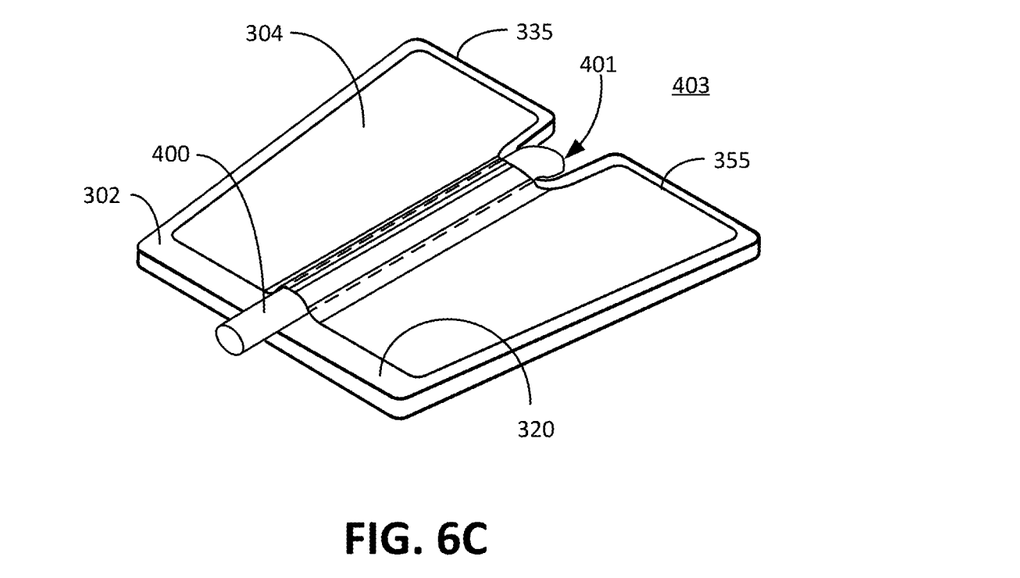
Figure 6D:
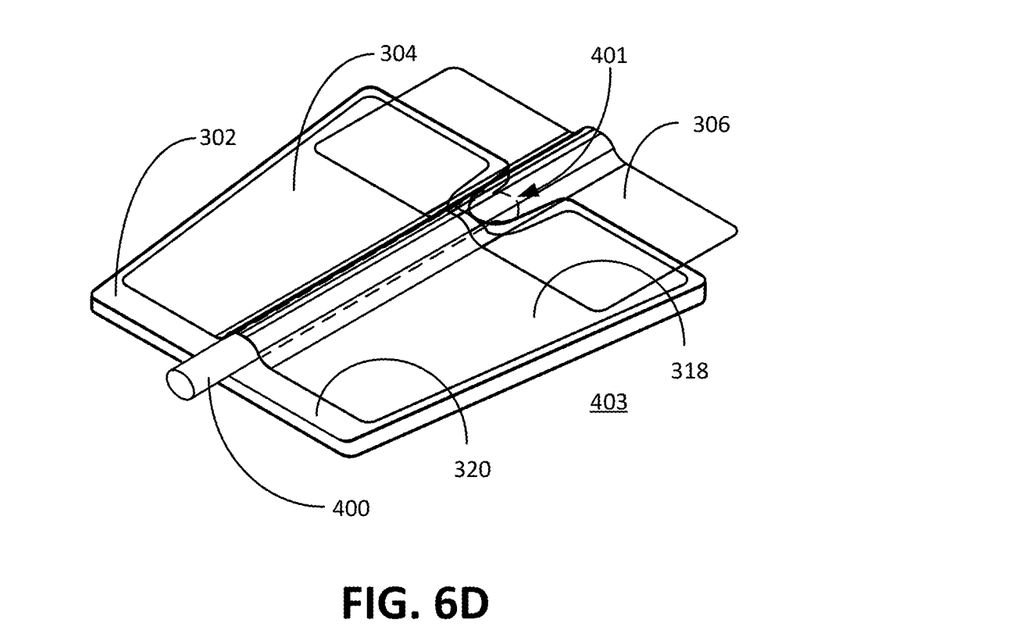

FIGS. 6A-6D illustratively depict a method for stabilizing a chest tube consistent with embodiments of the present invention. As shown in FIG. 6A, the flexible substrate 302 is adhered to a human chest wall 403 whereby an incision 401 sized for a chest tube 400 is exposed via the substrate U-shaped notch 305. In other words, the U-shaped notch 305 frames the incision 401, whereby the incision 401 is at least partially surrounded by the U-shaped notch 305 without, or essentially without, covering any part of the incision 401, as shown. In certain embodiments the flexible substrate 302 is attached to the chest wall 403 prior to cutting the incision 401 in the space provided by the U-shaped notch 305. Other embodiments contemplate the incision 401 first being made and then the flexible substrate 302 being placed over the incision, however adhering the flexible substrate 302 to the chest wall 403 may be compromised due to the blood from the incision 401.

FIG. 6B illustratively depicts the chest tube 400 inserted in the chest wall 403 via the incision 401 and bent down to be in contact with the top surface 320 of the flexible substrate 302. As shown, the substrate U-shaped notch 305 provides unobstructed access to the incision 401. Also as shown, the U-shaped notch 305 is a butting edge 331 that in some embodiments butts up against the chest tube 400 while in other embodiments the U-shaped notch 305 is simply in close proximity but not in contact with the chest tube 400. In this embodiment, the flexible substrate 302 accommodates at least the diameter of the chest tube 400 but does not close around the chest tube 400 whatsoever. In other words, the notch width 330 remains greater than the chest tube diameter as the U-shaped notch 305 approaches the front side/edge 342. This provides an added vantage of simplicity over prior art elements that close around a tube.

FIG. 6C illustratively depicts adhering the intermediate flexible membrane 304 to the top surface 320 of the flexible substrate 302 thereby retaining or otherwise locking in place the chest tube 400 in position. The chest tube 400 is depicted with dashed lines in the portion that is covered up by the intermediate flexible membrane 304. Certain embodiments contemplate that the intermediate flexible membrane 304 is sized to provide chest tube retention strength similar to that obtained by a scenario of suturing the chest tube to the incision. As also depicted in the present embodiment, the intermediate membrane periphery 355 is smaller than and remains inside of the substrate periphery 335. Certain embodiments envision that the intermediate flexible membrane 304 is within 1 cm the same shape as the flexible substrate 302. Other embodiments envision the intermediate flexible membrane 304 having a range between 50% the size of the flexible substrate 302 up to 100% of the size of the flexible substrate 302. This facilitates removal of the Sutureless Adhesion System 300 by simply pulling up on the flexible substrate 302. Certain embodiments envision that this could be made easier by a nonadhesive tab extending from the substrate periphery 335. Other embodiments envision that the substrate periphery 335 is the same size as the intermediate membrane periphery 355. Some embodiments envision the intermediate flexible membrane 304 exceeding the periphery size of the flexible substrate 302 so long as the membrane notch 310 does not eclipse or otherwise cover the substrate notch 305. While other embodiments envision the intermediate flexible membrane 300 and 4B integrated with the clear coversheet 306.

FIG. 6D illustratively depicts the configuration of FIG. 6C but with the clear flexible coversheet 306 covering at least a portion of the top substrate surface 320 and a portion of the top membrane surface 318. As shown, the clear flexible coversheet 306 covers the incision 401 and the chest tube 400 going into the incision 401. The clear flexible coversheet 306 also covers a portion of the human skin 415.

With continued reference to the intermediate flexible membrane 304 being sized to provide chest tube retention strength similar to that obtained by a scenario of suturing the chest tube to the incision. Certain embodiments envision determining retention strength by establishing the tensile strength of the suture material (note: there are multiple types of suture material including silk and nylon, suture sizes, and suture brands) and not the tearing strength of the skin 415 for at least the reason that the act of putting in a suture is variable between operators.

In one example, size 0 and 2-0 polyamide (nylon) sutures from Ethicon Inc., headquartered in Somerville, N.J. were used to establish a baseline tensile strength. Based on five samples tested, the average of the size 0 sutures (larger diameter) had an average breaking strength of 6.99 pound-force (lbf) and the size 2-0 had an average breaking strength of 5.43 lbf. The average combined breaking strength was 6.05 lbf with a standard deviation of approximately 0.99 lbf. From an engineering point of view, three standard deviations should account for 99.73% of the data. Thus, force of 9.02 lbf, of simply 9 lbf, is assumed to account for the majority of suture breaking forces measured for these suture elements. Accordingly, 9 lbf serves as the example input breaking strength for the Sutureless Adhesion System 300.

Figuring out the area of the flexible substrate 302 and the intermediate flexible member 304 is a classic calculus problem including changing force vectors with both sheer force of the adhesive sheet and tension force of the adhesive sheet. Based on whatever model or iteration is used for bonding failure due to the tube being pulled upwards and orthogonal to the Sutureless Adhesion System 300 when using the 9 lbf from above, a person skilled in the art can calculate the appropriate area of both the flexible substrate 302 and the intermediate flexible membrane 304. Current calculations indicate, depending on the adhesive used, that the area of the flexible substrate 302 should be between 10 in$^2$ and 60 in$^2$. Hence, at least a membrane area (of the intermediate flexible membrane 304) is determined by the membrane separation force of the intermediate flexible membrane 304, which is the force that causes the adhesion between the intermediate flexible membrane 304 to separate from the flexible substrate 302. This assumes that the intermediate flexible membrane 304 is smaller than the flexible substrate 302 and the adhesive strength of the intermediate flexible membrane 304 is approximately the same as the adhesive strength of the flexible substrate 302. The membrane separation force should be equal to or greater than the traditional strength of the sutured system. The traditional strength of the sutured system is the force of which sutured tube is pulled out or otherwise broken from the incision.

With the present description in mind, some additional embodiments of the present invention are provided below within the scope and spirit of the present invention.

For example, certain embodiments envision a sutureless adhesion system 300 comprising: a flexible skin adhering substrate 302 defined by a skin adhering substrate surface 322, a top substrate surface 320 and a substrate periphery 335, the substrate periphery 335 comprising a substrate incision framing notch 305 at a substrate butting edge 342, the substrate incision framing notch 305 sized to accommodate a chest tube diameter 441 defined by a chest tube 400, the substrate incision framing notch 305 defined by a substrate notch length 332 and a substrate notch width 331 greater than the chest tube diameter 441, the substrate incision framing notch 305 configured to frame an incision in human skin 415 through which the chest tube 400 is adapted to penetrate; an intermediate flexible non-skin contacting membrane 304 defined by a bottom membrane surface 316, a top membrane surface 318 and a membrane periphery 355, the bottom membrane surface 316 configured to only cover a portion of the flexible substrate 302 and the chest tube 400 when in the incision 401; a flexible cover sheet 306 defined by a bottom sheet surface 312, a top sheet surface 314 and a sheet periphery 319, the bottom sheet surface 312 is adapted to cover a portion of the top substrate surface 320 and the bottom sheet surface 312 adapted to cover at least a portion of the top membrane surface 318; adhesive covering at least a portion of the bottom substrate surface 322, the bottom membrane surface 316, and the bottom sheet surface 312, the flexible substrate 322 adapted to adhere to human skin.

The sutureless adhesion system is further envisioned wherein the intermediate flexible membrane 304 further comprising a membrane notch 310 that is wider than the substrate notch width 330. Certain embodiments further envision the membrane notch 310 comprises a membrane notch length 352 that is equal to or less than the substrate notch length 332, the membrane notch 310 frames the substrate notch 305 when the intermediate flexible non-skin contacting membrane 304 is attached to the flexible skin adhering substrate 302. While other embodiments further envision the substrate incision framing notch 305 is located at a substrate butting edge 331, no portion of the intermediate flexible non-skin contacting membrane 304 covers the substrate butting edge 331.

The sutureless adhesion system is further envisioned wherein the intermediate flexible non-skin contacting membrane 304 is within 1 cm of having an identical shape as the flexible skin adhering substrate 302.

The sutureless adhesion system is further envisioned wherein the flexible cover sheet 306 is adapted to constrain the chest tube 400 in place when covering the top membrane surface 318 when the chest tube 400 is in the incision 401.

The sutureless adhesion system is further envisioned wherein the Sutureless Adhesion System 300 consists of the flexible substrate 302, the intermediate flexible membrane 304 and the flexible cover sheet 306.

The sutureless adhesion system is further envisioned wherein the substrate periphery 335 is essentially a trapezoidal shape is defined by two parallel sides, a longer of the two parallel sides defines a butting edge.

The sutureless adhesion system is further envisioned wherein the flexible substrate is at least 2.5 inches in length and 2.5 inches in width.

The sutureless adhesion system is further envisioned wherein the flexible skin adhering substrate 302 possesses adhesive-1, the intermediate flexible non-skin contacting membrane 304 possesses adhesive-2 and the flexible cover sheet 306 possesses adhesive-3, the adhesive-1, the adhesive-2 and the adhesive-3 are not identical adhesive.

Certain other embodiments envision a method for stabilizing a chest tube 400, the method comprising: providing a flexible substrate 302 defined by a bottom substrate surface 322, a top substrate surface 320 and a substrate periphery 335, the flexible substrate 302 possessing a substrate U-shaped notch 305, substrate adhesive disposed on the bottom substrate surface 322; adhering the flexible substrate 302 via the substrate adhesive to human skin 415, the substrate U-shaped notch 305 providing unobstructed access to an incision 401 into a human chest wall 403 in the human skin 415 by framing the incision 401; placing the chest tube 400 on the top substrate surface 320 when one end of the chest tube 400 is disposed in the human chest 403 via the incision 401; securing the chest tube 400 to the top substrate surface 320 with an intermediate flexible membrane 304 by way of an adhesive covered bottom membrane surface 316, the membrane adhesive is not on a top membrane surface 318, the intermediate flexible membrane 304 possessing a membrane U-shaped notch 310 that frames the substrate U-shaped notch 305, the intermediate flexible membrane 304 does not extend beyond the substrate periphery 335; covering a portion of a top membrane surface 318 of the intermediate flexible membrane 304, the substrate U-shaped notch 310 and a portion of the human skin 315 with a bottom sheet side 312 of a flexible cover sheet 360, the bottom sheet side 312 comprising cover sheet adhesive.

The method for stabilizing a chest tube 400 is further envisioned with no elements other than the flexible substrate 302, the chest tube 400, the intermediate flexible membrane 304 and the cover sheet 306 are used in the method.

The method for stabilizing a chest tube 400 is further envisioned wherein there is nothing between the chest tube 400 and the flexible substrate 302.

The method for stabilizing a chest tube 400 is further envisioned wherein the membrane U-shaped notch 310 is wider than the substrate U-shaped notch 305.

The method for stabilizing a chest tube 400 is further envisioned wherein the intermediate flexible membrane 304 is between 50% and 100% the size of the flexible substrate 302.

The method for stabilizing a chest tube 400 is further envisioned wherein a membrane area of the intermediate flexible membrane 304 is proportional to a membrane separation force of the intermediate membrane 304, the membrane separation force is equivalent to a suture strength force required to pull the chest tube 400 from the human skin 415 when sutured thereto.

Yet other certain other embodiments envision a method for fixing a chest tube by providing a flexible substrate pad 302 possessing a substrate U-shaped notch 305 located at a substrate pad edge 342; positioning the substrate U-shaped notch 305 over an incision 401 in a human chest 403; adhering the flexible substrate pad 302 to human skin 415, the substrate U-shaped notch 305 unobstructedly (without obstructing) framing the incision 401; inserting the chest tube 400 in the incision 401; securing the chest tube 400 to the substrate pad 302 with an adhesive covered intermediate flexible membrane 304, nothing is between the chest tube 400 and the flexible substrate pad 302 when secured (nothing other than empty space/air), the flexible membrane 304 does not extend onto the human skin 415 or over any portion of the substrate pad edge 335; and covering a portion of the intermediate flexible membrane 304 over the substrate U-shaped notch 305 and a portion of the human skin 415 with an adhesive coated flexible cover sheet 306.

The method of method for fixing a chest tube is further envisioned wherein the intermediate flexible membrane 304 possesses a membrane U-shaped notch 310 that frames the substrate U-shaped notch 305.

The method of method for fixing a chest tube is further envisioned wherein there are no other elements other than the chest tube 400 between the flexible substrate pad 302 and the flexible cover sheet 304.

While still other certain embodiments envision a sutureless adhesion apparatus 300 comprising: a flexible skin adhering substrate 302 defined by a skin adhering substrate surface 322, a top substrate surface 320 and a substrate periphery 335, the substrate periphery 335 comprising a substrate incision framing notch 305 at a substrate butting edge 342, the substrate incision framing notch 305 unobstructely frames an incision 401 that is capable of being made in human skin 415, a chest tube 400 extending from the incision 401; an intermediate flexible non-skin contacting membrane 304 defined by a bottom membrane surface 316 with adhesive, a top membrane surface 318 and a membrane periphery 355, the bottom membrane surface 316 adhered to and covering nothing other than a portion of the flexible substrate 302 and a portion of the chest tube 400; a flexible cover sheet 306 defined by a bottom sheet surface 312, a top sheet surface 314 and a sheet periphery 319, the flexible cover sheet 306 adhered at least a portion of the top substrate surface 320 and at least a portion of the top membrane surface 318, the skin adhering substrate surface 322 and a portion of the bottom sheet surface 312 configured to adhere to human skin 415.

The sutureless adhesion apparatus is further envisioned wherein the apparatus between the flexible skin adhering substrate 302 and the flexible cover sheet 406 consists of the chest tube 400 and the intermediate flexible non-skin contacting membrane 304.

The sutureless adhesion apparatus is further envisioned wherein the membrane U-shaped notch 310 is wider than the substrate U-shaped notch 305.

The sutureless adhesion apparatus is further envisioned wherein the intermediate flexible membrane 304 is between 50% and 100% the size of the flexible substrate 302.

The sutureless adhesion apparatus is further envisioned wherein a membrane area of the intermediate flexible membrane 304 is proportional to a membrane separation force, which is equivalent to a suture strength force required to pull the chest tube 400 from the human skin 415 when sutured thereto.

The above embodiments are not intended to be limiting to the scope of the invention whatsoever because as a skilled artisan will recognize, there are many more embodiments easily conceived within the teachings and scope of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, though a chest tube 400 is depicted is the only element held in place by the Sutureless Adhesion System 300, other elements such as the cannula 140 of FIG. 1A can be similarly used without departing from the scope and spirit of the present invention. Another example can include providing various other shaped flexible substrates, intermediate flexible membranes and flexible cover sheet without departing from the scope and spirit of the present invention. Though embodiments of the present invention are directed to a person and person's skin 415, it is envisioned that the embodiments could be used with animals in similar situations while staying within the scope and spirit of the present invention. Yet another example includes adhesive being applied to only a portion of the bottom surfaces and not on the entire surfaces as exemplified in the above description. Further, the terms "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed and as defined in the appended claims.

What is claimed is:

1. A sutureless adhesion system comprising:
a flexible skin adhering substrate defined by a skin adhering substrate bottom surface, a top substrate surface and a substrate periphery, the substrate periphery comprising a substrate incision framing notch at a substrate butting edge, the substrate incision framing notch sized to accommodate a chest tube diameter defined by a chest tube, the substrate incision framing notch defined by a substrate notch length and a substrate notch width greater than the chest tube diameter, the substrate incision framing notch configured to frame an incision in human skin through which the chest tube is adapted to penetrate;
an intermediate flexible non-skin contacting membrane defined by a bottom membrane surface, a top membrane surface and a membrane periphery, the bottom membrane surface configured to only cover a portion of the flexible substrate and the chest tube when in the incision;
a flexible cover sheet defined by a bottom sheet surface, a top sheet surface and a sheet periphery, the bottom sheet surface adapted to cover at least a portion of the top substrate surface and at least a portion of the top membrane surface;
adhesive covering at least a portion of the bottom substrate surface, the bottom membrane surface, and the bottom sheet surface, the flexible substrate adapted to adhere to human skin.

2. The sutureless adhesion system of claim 1 wherein the intermediate flexible membrane further comprising a membrane notch that is wider than the substrate notch width.

3. The sutureless adhesion system of claim 2 wherein the membrane notch comprises a membrane notch length that is equal to or less than the substrate notch length, the membrane notch frames the substrate notch when the intermediate flexible non-skin contacting membrane is attached to the flexible skin adhering substrate.

4. The sutureless adhesion system of claim 2 wherein the substrate incision framing notch is located at a substrate butting edge, no portion of the intermediate flexible non-skin contacting membrane covers the substrate butting edge.

5. The sutureless adhesion system of claim 1 wherein the intermediate flexible non-skin contacting membrane is within 1 cm of having an identical shape as the flexible skin adhering substrate.

6. The sutureless adhesion system of claim 1 wherein the flexible cover sheet is adapted to constrain the chest tube in place when covering the top membrane surface when the chest tube is in the incision.

7. The sutureless adhesion system of claim 1 wherein the Sutureless Adhesion System consists of the flexible substrate, the intermediate flexible membrane and the flexible cover sheet.

8. The sutureless adhesion system of claim 1 wherein the substrate periphery is essentially a trapezoidal shape is defined by two parallel sides, a longer of the two parallel sides defines a butting edge.

9. The sutureless adhesion system of claim 1 wherein the flexible skin adhering is at least 2.5 inches in length and 2.5 inches in width.

10. The sutureless adhesion system of claim 1 wherein the flexible skin adhering substrate bottom surface possesses adhesive-1, the intermediate flexible non-skin contacting membrane possesses adhesive-2 and the flexible cover sheet possesses adhesive-3, the adhesive-1, the adhesive-2 and the adhesive-3 are not identical adhesive.

11. The sutureless adhesion system of claim 1 wherein intermediate flexible non-skin contacting membrane only contacts the chest tube and the top substrate surface of the flexible skin adhering substrate.

12. A method for stabilizing a chest tube, the method comprising:
providing a flexible substrate pad possessing a substrate U-shaped notch located at a substrate pad edge;
positioning the substrate U-shaped notch over an incision in a human chest;
adhering the flexible substrate pad to human skin, the substrate U-shaped notch unobstructedly framing the incision;
inserting the chest tube in the incision;
securing the chest tube to the substrate pad with an adhesive covered intermediate flexible membrane, nothing is between the chest tube and the flexible substrate pad when secured, the flexible membrane does not extend onto the human skin or over any portion of the substrate pad edge; and
covering a portion of the intermediate flexible membrane over the substrate U-shaped notch and a portion of the human skin with an adhesive coated flexible cover sheet.

13. The method of claim 12 wherein the intermediate flexible membrane possesses a membrane U-shaped notch that frames the substrate U-shaped notch.

14. The method of claim 12 wherein the intermediate flexible membrane is between 50% and 100% the size of the flexible substrate.

15. The method of claim 12 wherein there are no other elements other than the chest tube between the flexible substrate pad and the flexible cover sheet.

16. A sutureless adhesion apparatus comprising:
a flexible skin adhering substrate defined by a skin adhering substrate bottom surface, a top substrate surface and a substrate periphery, the substrate periphery comprising a substrate incision framing notch at a substrate butting edge, the substrate incision framing notch unobstructely frames an incision that is capable of being made in human skin, a chest tube extending from the incision;
an intermediate flexible non-skin contacting membrane defined by a bottom membrane surface with adhesive, a top membrane surface and a membrane periphery, the bottom membrane surface adhered to and covering nothing other than a portion of the flexible substrate and a portion of the chest tube;
a flexible cover sheet defined by a bottom sheet surface, a top sheet surface and a sheet periphery, the flexible cover sheet adhered at least a portion of the top substrate surface and at least a portion of the top membrane surface,
the skin adhering substrate surface and a portion of the bottom sheet surface configured to adhere to human skin.

17. The apparatus of claim 16 wherein the apparatus between the flexible skin adhering substrate and the flexible cover sheet consists of the chest tube and the intermediate flexible non-skin contacting membrane.

18. The apparatus of claim 16 wherein the membrane U-shaped notch is wider than the substrate U-shaped notch.

19. The apparatus of claim 16 wherein the intermediate flexible membrane is between 50% and 100% the size of the flexible substrate.

20. The apparatus of claim 16 wherein a membrane area of the intermediate flexible membrane is proportional to a membrane separation force of the intermediate membrane, the membrane separation force is equivalent to a suture strength force required to pull the chest tube from the human skin when sutured thereto.

\* \* \* \* \*